United States Patent [19]

Strickland

[11] Patent Number: 5,661,125
[45] Date of Patent: Aug. 26, 1997

[54] STABLE AND PRESERVED ERYTHROPOIETIN COMPOSITIONS

[75] Inventor: Thomas Wayne Strickland, Moorpark, Calif.

[73] Assignee: AMGEN, Inc., Thousand Oaks, Calif.

[21] Appl. No.: 448,960

[22] Filed: May 24, 1995

Related U.S. Application Data

[63] Continuation of Ser. No. 156,609, Nov. 23, 1993, which is a continuation of Ser. No. 926,773, Aug. 6, 1992, abandoned.

[51] Int. Cl.$^6$ .................................................. A61K 38/22
[52] U.S. Cl. .................................................................. 514/8
[58] Field of Search ...................................... 514/8

[56] References Cited

U.S. PATENT DOCUMENTS

| | | |
|---|---|---|
| 4,806,524 | 2/1989 | Kawaguchi et al. . |
| 4,879,272 | 11/1989 | Shimoda et al. ............................. 514/8 |
| 4,992,419 | 2/1991 | Woog et al. . |
| 5,322,837 | 6/1994 | Hewick et al. ............................. 514/8 |
| 5,354,934 | 10/1994 | Pitt et al. ........................................ 514/8 |
| 5,376,632 | 12/1994 | Konings et al. ............................. 514/8 |

FOREIGN PATENT DOCUMENTS

| | | |
|---|---|---|
| 190823 | 8/1991 | Japan . |
| WO91/11200 | 8/1991 | WIPO . |
| 91-190823 | 8/1991 | Japan . |

OTHER PUBLICATIONS

Aalto, et al, "p–Hydroxybenzoic Acid Esters as Preservatives; I. Uses, Antibacterial and Antifungal Studies, Properties and Determination," *Journal of American Pharm. Assoc.*, 8(16):449–457 (1953).
Akers, M., "Considerations in Selecting Antimicrobial Preservative Agents for Parenteral Product Development," *Pharm Tech*, pp. 36–46 (May) (1984).
Aldrete, et al "Allergy to Local Anesthetics," *JAMA*, 207(2):356–357 (1969).
Alegnani, W., "A Rapid Test for Evaluating the Preserving Properties of Multidose Injectables," *Inter. Symp. on Preserv., Devel. Biol. Standard*, 24:91–97 (1974).
Ashford, et al, "A Study of the Effectiveness of Vaccines. Antimicrobial Agents in Biological Parenteral Products," *Intern Symp. on Preserv., Devel. Biol. Standard*, 24:29–38 (1973).
Behme et al, "Incompatibility of Ifosfamide with Beyzy-1–Alcohol Preserved Bacteriostatic Water for Injection," *Am. J. Hosp. Pharm*, pp. 627–628 (1988).
Davisson, et al., "The Preservation of Polcomyelitis Vaccine With Stabilized Merthcolate," *J. Lab. Clin. Med.*, 4/(1):8–19 (1956).
Decker, et al., "Frequency of Preservative Use in Cosmetic Formulas as Disclosed to FDA–1987," *Cosmetics & Toiletries*, 102:21–24 (1987).
Geigert, J., "Overview of the Stability and Handling of Recombinant Protein Drugs," *Journal of Parenteral Science & Tech.*, 43(5):220–224 (1989).

Gershanik, et al., "The Gasping Syndrome and Benzyl Alcohol Poisoning," *N.E. Journal of Med.*, pp. 1384–1388 (Nov. 1982).
Gershenfeld, et al., "Preservatives for Preparations Containing Gelatin," *Am. J. Pharm*, 111:277–287 (1939).
Gottfried, N.S., "Alkyl p–Hydroxybenzoate Esters as Pharmaceutical Preservatives," *Am. J. Hosp. Pharm.*, 19:310–314 (1962).
Happel, J., "Antimicrobial Preservatives in Pharmaceuticals," *Disinfection Steriliz. and Preservation*, pp. 579–588 (1972).
Jaconia, D., "Preservatives in Pharmaceutical Products," *Quality Control in Pharm. Industry*, 1:101–128 (1972).
Kimura, et al., "Parenteral Toxicity Studies With Benzyl Alcohol," *Toxicology and Applied Pharm.*, 18:60–68 (1971).
Kostenbauder, "Physical Factors influencing the Activity of Antimicrobial Agents," *Disinfection, Sterilization, Preservation*, pp. 811–828 (1983).
Lachman, L., "Instability of Antimicrobial Preservatives," *Meeting of Parenter, Drug Assn.*, pp. 127–144 (Jun. 1967).
McDavid, J., "Characteristics of Parabens as Preservatives," *Intern Sympos. on Preserv., Develop Biol. Standard*, 24:49–55 (1973).
Miyake, et al., "Purification of Human Erythropoietin," *Journal of Biol. Chemistry*, 252(15):5558–5564 (1977).
Nagel. et al., "Paraben Allergy," *JAMA*, 237(15):1594–1595 (1977).
Perlman, et al., "Formula and Strategy for Recombinant Proteins: HGH and PA", *Genentech Inc.*, pp. 23–30 (1988).
Russell, D., "The Inclusion of Antimicrobial Agents in Pharmaceutical Products," *Adv. Appl. Micro.*, 9:1–38 (1967).
Russell, D., "Principals of Antimicrobial Activity," *Disinfection, Sterilization, Preservation*, pp. 717–750 (1983).
Shmunes, E., "Allergic Dermatitis to Benzyl Alcohol in Injectable Solution," *Arch Dermatol*, 120:1200–1201 (1984).
Strickland, et al., "Occurrence of Sulfate on the N–Linked Oligosaccharides of Human Erythropoietin," *Journal of Cell Bioch. Suppl.*, 16(d):167 (1992).
Wallhausser, K., "Antimicrobial Preservatives in Europe: Experience With Preservatives Used in Pharmaceuticals and Cosmetics," *International Symp. on Preserv. in Biol. Products, Devel. Biol. Standard*, 24:9–28 (1973).
Yu–Chang, et al., "Review of Excipients and pH's for Parenteral Products Used in the United States" *Journal of Parenteral Durg Assoc.*, 34(6):452–462 (1980).
Remington's Pharmaceutical Science, 1975, p. 1466.

*Primary Examiner*—Rebecca Cook
*Attorney, Agent, or Firm*—Stuart L. Watt; Steven Odre; Ron Levy

[57] ABSTRACT

The invention is to stable compositions of erythropoietin that contain an antimicrobial preservative thereby providing a multi-dose formulation. Preservatives useful in the pharmaceutical compositions of the present invention include benzyl alcohol, parabens, phenol and mixtures thereof. Other additives, including buffers may be included in the composition.

24 Claims, No Drawings

STABLE AND PRESERVED ERYTHROPOIETIN COMPOSITIONS

This application is a continuation of application Ser. No. 08/156,609, filed Nov. 23, 1993, which is a continuation of application Ser. No. 07/926,773 filed on Aug. 6, 1992, which has been abandoned.

BACKGROUND OF THE INVENTION

The present invention relates to stable and preserved erythropoietin pharmaceutical compositions that provide convenience of use and ease of administration.

Erythropoietin is a glycoprotein hormone that stimulates the formation of red blood cells. Erythropoietin is produced in the kidney, and once produced, it circulates to the bone marrow where it stimulates the conversion of primitive precursor cells into proerythroblasts which subsequently mature into red blood cells. In the normal healthy state, erythropoietin is present in very low concentrations in plasma, i.e., about 0.01 to 0.03 U/ml, but when the level of oxygen in transport is reduced, a condition known as hypoxia, the kidney produces more erythropoietin. Hypoxia can be the result of loss of large amounts of blood, destruction of red blood cells by radiation, or exposure to high altitudes. In addition, various forms of anemia cause hypoxia since red blood cells are responsible for oxygen transport in the body. In the normal state, an increased level of erythropoietin stimulates the production of new red blood cells thereby raising the level of oxygen and reducing or eliminating the hypoxic condition.

In contrast to this correction of hypoxia which occurs normally, patients with chronic renal failure ("CRF") have limited or no production of erythropoietin, and consequently, do not produce sufficient red blood cells. As the normal life span for red blood cells is about 120 days, such patients become increasing anemic with time. Prior to the development of recombinant erythropoietin, patients with chronic renal failure often had to undergo regular blood transfusions to maintain a minimum level of red blood cells.

The production of human erythropoietin outside the body using recombinant DNA technology is described in U.S. Pat. No. 4,703,008 to Lin and assigned to Amgen Inc., the assignee hereof. Recombinant human erythropoietin (rEPO) is produced by mammalian cells into which the human erythropoietin gene has been introduced. These cells produce a polypeptide product which has the identical amino acid sequence of isolated natural erythropoietin. Moreover, this rEPO has been shown to have the same biological effects as endogenous erythropoietin even though rEPO is known to have a different carbohydrate composition than naturally occurring erythropoietin (Strickland et al, *J. Cell. Biochem.*, Supplement 16D, P324, 1992). rEPO has proven to be extremely effective in treating various forms of anemias, especially that associated with end stage renal disease. The administration of rEPO, as replacement therapy for the missing protein, significantly reduces or eliminates the need for blood transfusions in most CRF patients. Similarly, rEPO has proven to be effective in treating other types of anemia including that associated with the treatment of AIDS using AZT.

Amgen has sold rEPO in the United States for research purposes since 1985, and for therapeutic purposes since June 1989. Amgen manufactures rEPO which has been given the proper name of Epoetin alfa. Epoetin alfa is sold by Amgen under the trademark EPOGEN® and by Ortho Pharmaceutical under the trademark PROCRIT®. Epoetin alfa is formulated and sold as an aqueous solution of rEPO containing sodium citrate buffer to maintain the solution at about pH 7, human serum albumin (HSA), sodium chloride, and water for injection, USP. The use of HSA in rEPO formulations was first disclosed in Lin, U.S. Pat. No. 4,703,008, Col. 35 lines 17–20. The current formulation of Epoetin alfa contains no antimicrobial preservative and is sold in vials designated as "single-use" and containing 2,000, 3,000, 4,000 or 10,000 U/ml of rEPO. Epoetin alfa is an injectable product approved for administration by either intravenous or subcutaneous routes.

In evaluating the use of Epoetin alfa, certain needs have been discovered regarding its formulation and delivery. First, it has been reported that some patients experience local discomfort or stinging upon the subcutaneous administration of Epoetin alfa. In a study reported by Frenken, L., et al. in *British Medical Journal*, 1991; 303:288, on the use of Exprex®, a rEPO product produced by Cilag GMBH which is formulated identically to Epoetin alfa, a number of patients experienced a burning or itching after subcutaneous injection. Ameliorating this stinging effect without decreasing the ease of administration is highly desired. Second, being an injectable product, some users and caregivers would greatly benefit by being able to draw several doses from a single vial, i.e., a multi-dose product as opposed to a single-dose. In order for a pharmaceutical product to be multi-dose it must contain an antimicrobial agent in order to kill or inhibit the growth of any microbes which may inadvertently be introduced into the container. This prevents the growth and subsequent administration of such microbes to the patient. For some, a multi-dose rEPO would reduce handling and inventory while eliminating waste of a valuable product. The combination of a non-sting and multi-dose, ready-to-use solution formulation is highly desirable and meets several needs of the patient and caregiver.

In order to be commercially useful, the pharmaceutical composition must be stable. Others have suggested different formulations of rEPO which are reported to be stable, but none contain a preservative thereby providing multi-dose capability. The literature suggests and illustrates the relative instability of erythropoietin in solution and the sensitivity of erythropoietin to various additives.

U.S. Pat. No. 4,806,524 to Kawaguchi and Shimoda discloses lyophilized and aqueous solution preparations containing erythropoietin and one or more stabilizers. Kawaguchi et al. report the need for stabilizers since "erythropoietin is an instable substance and the compound purified to a clinically acceptable level and formulated in a trace amount (≈ a few μg) that is suitable for a single dosage will be easily inactivated by such environmental factors as temperature and humidity." (Col.1, lines 15–20) Kawaguchi et al. reported testing erythropoietin derived from human urine with a long list of various "stabilizers". The results of stability for lyophilized formulation show fair stability, but the results for aqueous solutions show that the solutions are very instable. After only one week at 25° C., the solution formulations showed losses in residual activity of about 30% or more as measured by in vivo testing. (See Table in U.S. Pat. No. 4,806,524). The lyophilized forms showed greater stability after being exposed to 37° C. for one month, while still in the lyophilized form, but many of the formulations showed losses of 5–10% or more. The results of Kawaguchi et al. confirm their statement that erythropoietin is an "instable substance" especially in solution form and further reveal that when combined with known stabilizers, the resulting stability of the erythropoietin is varied and unpredictable.

In U.S. Pat. No. 4,879,272, Shimoda and Kawaguchi show an increase in recovery of erythropoietin by using additives to reduce the adsorption of erythropoietin onto the wall of a container. The results shown in the Table, using urinary erythropoietin with different additives and measured after only two hours at room temperature, however, report the rapid and varied loss of erythropoietin in solution. The values reported range from 69.2–98.8% recovery of erythropoietin for the solutions containing additives. While the results compare favorable to the recovery of only 16.5% with no additive, generally the loss is still very significant. However, as described in Experiments 1 and 2, this data reflects only the level of a radioactive labeled product and reveal nothing about the loss of erythropoietin to decomposition or whether the remaining product is active. As in U.S. Pat. No. 4,806,524, the data again reflects the different effects of different additives on erythropoietin.

Further, U.S. Pat. No. 4,992,419 to Woog et al. disclose lyophilized erythropoietin preparations that include a buffer, urea, a detergent and one or more of various amino acids. In addition, various other additives are suggested. In fact, Woog et al. state that the urea and amino acids are "decisive for stabilization." (Col. 2, lines 43–44). Urea is used in rather high amounts relative to the amount of erythropoietin, i.e., 5 to 50 g./liter and preferably 10–15 g./liter. The specified amino acids used in the formulation are glycine, L-alanine, L-arginine, L-isoleucine, L-leucine, L-phenylalanine, L-glutamic acid and L-threonine. In addition, a detergent or wetting agent are added to the composition to reduce the adhesion of erythropoietin to the walls of the vessel. At Col. 4, lines 3–8, Woog et al. report that aqueous solutions of erythropoietin having these additives are stable for about 1 year at 0° C. and only a few months at ambient temperatures. Although Woog et al. disclose various additives to be used in erythropoietin solutions, no suggestion is given concerning the use of a preservative.

In contrast to the formulations described in the above-cited U.S. Patents, Epoetin alfa has proven to be quite stable in solution form and it has an approved shelf-life of 24 months under refrigerated conditions, 2°–8° C., as approved by the United States Food and Drug Administration. Moreover, as a liquid, ready-to-use formulation, Epoetin alfa is more convenient to administer than a lyophilized formulation which must be reconstituted prior to administration. This reconstitution procedure is time consuming for the medical personnel involved, and it poses the risk of mishandling and improper reconstitution. For these reasons, among others, solution formulations are generally preferred over lyophilized ones.

Aside from the discussion above, very little has been reported concerning the stability of erythropoietin in solution, and nothing is disclosed concerning preserved formulations of erythropoietin. Also, since erythropoietin is one of the early recombinant proteins to be produced, nothing specific can be derived from the use of preservatives with other proteins that would suggest any particular preserved formulation for erythropoietin. See, e.g., Geigert, J., "Overview of the Stability and Handling of Recombinant Protein Drugs," *Journal of Parenteral Science & Technology*, Vol. 43, No. 5, 220–224 (1989). In that article, Geigert discusses the recombinant protein drugs approved for marketing by the FDA as of March 1989. Of the marketed recombinant drugs, two were sold as liquids and four as lyophilizates. (See Table VI of Geigert). The two liquid products have approved expiration dates of one and two years at 2°–8° C. Geigert also reports that for the lyophilized products reconstituted with a bacteriostat in the solution, the expiration dating for those solutions ranged from 7–30 days at 2°–8° C. (See Table VII). Moreover, Geigert reports that IL-2, a product which at this time was undergoing clinical trials, is not compatible with bacteriostatic agents.

Nothing can be drawn from the literature concerning a stable and preserved erythropoietin formulation. A need still exists for a such a formulation that would provide the benefits of a multi-dose solution formulation, and additionally that would avoid the discomfort or stinging sometimes associated with subcutaneous injection of certain solution formulations. The present invention provides such a formulation. In contrast to the formulations suggested by the above cited patents, the formulations of the present invention are multi-dose and stable for extended periods of time.

SUMMARY OF THE INVENTION

The present invention is directed to novel pharmaceutical compositions comprising a solution of a therapeutically effective amount of erythropoietin and an antimicrobial preservative. The composition preferably provides the dual benefits of being a multi-use or multi-dose solution and a reduction in the discomfort experienced by some patients upon injection of certain erythropoietin solution formulations. Surprisingly, the preferred solutions are storage stable for commercially useful lengths of time, especially under refrigerated conditions, 2°–8° C.

In a preferred embodiment, the preservative is selected from benzyl alcohol, parabens, phenol and mixtures thereof. Benzyl alcohol, which has the dual ability to preserve the solution and to act as a local anesthetic to alleviate injection site discomfort is especially preferred. The invention further comprises the use of a buffering agent, most preferably a citrate or phosphate buffer. The use of benzyl alcohol, or a similar preservative that also exhibits the aforementioned dual capability of local anesthetic and antimicrobial, is most preferred when the buffering agent is a citrate buffer.

Additional elements that provide preferred embodiments of the invention include the use of one or more of the following: an isotonicity adjusting agent; an anti-adsorbent; a pH adjusting agent; a pH maintained in the range of 5–8, and more preferably about 6; and the use of rEPO in the composition. Preferably, the composition remains in solution form from formulation until use, is ready to use by the caregiver or patient, and is not reconstituted from a lyophilizate. As would be understood by a person having knowledge of the art, the invention encompasses preserved erythropoietin solutions having various combinations of these additional elements.

DETAILED DESCRIPTION

The pharmaceutical compositions of the present invention are described in more detail in the discussion that follows and are illustrated by the examples provided below. The examples show various aspects of the invention and include results of stability testing and microbial challenge of samples maintained in vials for up to two years or more under both refrigerated conditions and under controlled room temperature. Some accelerated stability data at elevated temperatures is also reported. The results were surprising in that even with the addition of a preservative, the erythropoietin solutions were stable for several months at room temperature and for two years or more under refrigerated conditions, 2°–8° C.

When used with respect to pharmaceutical compositions, the term "stable" is generally understood in the art as meaning less than a certain amount, usually 10%, loss of the active ingredient under specified storage conditions for a stated period of time. The time required for a composition to be considered stable is relative to the use of each product and is dictated by the commercial practicalities of producing the product, holding it for quality control and inspection, shipping it to a wholesaler or direct to a customer where it is held again in storage before its eventual use. Including a safety factor of a few months time, the minimum product life for pharmaceuticals is usually one year, and preferably more than 18 months. As used herein, the term "stable" references these market realities and the ability to store and transport the product at readily attainable environmental conditions such as refrigerated conditions, 2°–8° C.

With respect to proteins such as erythropoietin, the stability of the active ingredient is important not only to ensure accurate dosing, but also to limit the potential generation of an antigenic form of the protein. For example, a 10% loss (90% potency of label) of erythropoietin may be acceptable considering dosing requirements, but it is acceptable as an injectable product only if the erythropoietin has not changed in such a way that potentially antigenic compounds such as aggregates or fragments are present in the composition.

As the active ingredient in the pharmaceutical compositions of the present invention., it is preferred to use erythropoietin having the amino acid sequence of human erythropoietin, or closely related analogues thereof. The erythropoietin may be produced by mammalian cells outside of the body, or it may be isolated from natural sources. Preferably, the erythropoietin is recombinant erythropoietin ("rEPO"), i.e., erythropoietin produced using recombinant DNA technology in which a host cell is transfected with a DNA sequence encoding human erythropoietin as described in U.S. Pat. No. 4,703,008 to Lin. The preferred host cells are Chinese Hamster Ovary ("CHO") cells as described in Example 10 of the Lin patent. Other host cells known in the art, e.g. baby hamster kidney cells, may also be used to produce erythropoietin useful in the present invention. While the procedures of Example 10 of the Lin patent are the preferred method for producing rEPO, modifications and changes could be made to that process as known in the art.

The erythropoietin is present in the compositions in therapeutically effective amounts. The package insert for Epoetin alfa indicates that the therapeutic range is about 50–300 Units/kg given three times a week. The recommended starting dose is 50–100 u/kg administered three times a week. The effect of Epoetin alfa is monitored by measuring the hematocrit with the target hematocrit range being 30–33%. Dose adjustment is made by monitoring the hematocrit. The single use vials of Epoetin alfa contain 2,000, 3,000 4,000 or 10,000 units of rEPO. As the formulations of the present invention are preserved and provide the benefit of being multi-dose, the formulations preferably will contain many times the number of units of rEPO present in a single-use vial. Compositions containing 1,000–100,000 units or more of rEPO per vial are included within the present invention.

The preservatives useful in the compositions of the present invention are those preservatives compatible with erythropoietin so that the compositions are stable. Particular preservatives contemplated for use include benzyl alcohol, parabens, phenol, phenol derivatives, benzalkonium chloride and mixtures thereof. Depending on the particular preservative utilized, the amount of preservative could vary. In a preferred embodiment, benzyl alcohol is used in the amount of 0.6–2.0%, and most preferably, about 1%. At this concentration, benzyl alcohol provides the preservative and the local anesthetic capacities without unduly affecting the stability of the erythropoietin.

Among the parabens, the ones preferred for use in the compositions of the present invention are methyl paraben, propyl paraben, and butyl paraben. The parabens may be used as a preservative singly or, in a most preferred embodiment, as a mixture of methyl and propyl paraben. The total content of parabens is preferably within the range 0.05–0.3%, more preferably with an amount of about 0.2% being most preferred. A most preferred paraben preservative is about 0.15–0.20% methyl paraben in combination with about 0.01–0.03% propyl paraben. Among the examples shown below is a combination of 0.18% methyl paraben with 0.02% propyl paraben. The use of a mixture of parabens and 0.5% benzyl alcohol as a preservative is also illustrated in the examples.

Concerning the use of phenol as a preservative, it may be used in amounts ranging from 0.2% to 0.5% with 0.3% being preferred. Other derivatives of phenol, in addition to the ones mentioned above, also may be used as preservatives. As examples of such derivatives, metacresol (m-cresol) and chlorocresol are used in compositions shown below, but the accelerated stability data with these compounds showed more rapid decay of the rEPO than was observed with the other preservatives mentioned above.

The erythropoietin compositions preferably include a buffering agent to maintain the pH of the solution within a desired range. Preferred agents include various salt, acidic, or basic forms of the following anions: citrate, phosphate, tartrate, succinate, adipate, maleate, lactate, acetate, bicarbonate, and carbonate. Representative salts of these buffers which may be used are the sodium and potassium forms, as long as the salt and the amount are physiologically compatible in an injectable composition. Mixtures of these buffering agents may also be used. Among these agents, citrate and phosphate buffers are the most preferred.

The amount of buffering agent useful in the pharmaceutical compositions depends largely on the particular buffer used and the pH of the solution. For example, citrate is a more efficient buffer at pH 6 than at pH 7 so less citrate may be used in a solution at pH 6 than at pH 7. The preferred pH range for the solutions is 5–8 with 6–7 being more preferred, and a pH of about 6 being most preferred. Over these pH values, the amount of buffers will generally range from about 1 mM to about 30 mM. In a preferred embodiment, the amount of citrate buffer ranges from 1 mM to about 20 mM, and is preferably about 2–5 mM for a pH of about 6.

The compositions of the present invention may further include an isotonicity adjusting agent to render the solution isotonic and more compatible for injection. The preferred agents include sodium chloride, glycerol, mannitol, sucrose, sorbitol and mixtures thereof. The most preferred agent is sodium chloride.

The amount of isotonicity adjusting agent needed to render the solution isotonic varies with the particular agent but generally falls within the range of 0.1–10%.

The compositions of the present invention may further include an anti-adsorbent which acts to reduce the loss of erythropoietin by adsorption to the walls of the container and to other surfaces the product will contact, such as syringes and needles. Various surfactants and protein compounds such as albumin or gelatin may be used. The preferred anti-adsorbents are human serum albumin (HSA) and gelatin. These anti-adsorbents should be used in an amount sufficient to reduce the adsorption of erythropoietin to surfaces thereby increasing the stability in solution without otherwise negatively affecting the erythropoietin stability, e.g., causing aggregation or decomposition. A preferred amount of HSA is about 0.25%.

The following examples will illustrate in more detail the various aspects of the present invention.

Examples 1-6 and Comparative Example 1

Solution of rEPO, sodium citrate buffer, and various preservatives at pH 6 and pH 7 were prepared. The preservatives and the respective concentrations of preservatives used were the following:

| Example | Preservative |
|---------|-------------|
| 1. | 0.5% phenol |
| 2. | 0.5% m-cresol |
| 3. | 2% benzyl alcohol |
| 4. | 0.18% methyl paraben and 0.02% propyl paraben |
| 5. | 0.18% methyl paraben, 0.02% propyl paraben and 0.5% benzyl alcohol |
| 6. | 0.3% chlorocresol |

In addition, Comparative Examples 1 and 2 ("CE1" and "CE2") were preservative free controls to which no preservative was added. Stock solutions of each of these preservatives 1-6 and the comparative examples were prepared to contain final concentrations of sodium citrate buffer and sodium chloride in final concentrations of about 20 and 100 mM, respectively and having pHs of either approximately 6 or 7. The preservatives designated as 4-6 above were stirred overnight at room temperature to allow dissolution of the components. The rEPO test samples were prepared by mixing 4.455 ml of each of the preservative stock solutions and 45 µl of a 1,000,000 U/ml preparation of rEPO in 20 mM sodium citrate buffer, 100 mM sodium chloride, pH 7. The resulting concentration of rEPO was 10,000 U/ml in each of the test samples. The rEPO was produced by CHO cells in accordance with the procedures of Example 10 in U.S. Pat. No. 4,703,008 to Lin. For the CE1 and CE2, 125 µl of the concentrated EPO solution was added to 12.375 ml of each of the preservative free stock solutions (pH 6 and 7). The CE1 preparations were used with no further treatment. CE2 preparations were sterile filtered through a 0.22 micron filter prior to use. A second set of test samples was prepared similar to those described above but with the further addition of HSA. The HSA used was Albuminar-25, a 25% solution of HSA purchased from Armour Pharmaceuticals, and it was added in the amount of 45 µl to the preserved solutions, and 125 µl to the comparative example solutions so that the final HSA concentration in each of the second set of test samples was 0.25%. For example, a preservative containing sample would be made up of 45 µl of 25% HSA, 45 µl of 1,000,000 U/ml rEPO, and 4.41 ml of preservative containing solution at either pH 6 or pH 7. When making up the HSA containing samples, the chlorocresol was observed to cause some of the albumin to precipitate. As a result, the HSA containing chlorocresol solutions were removed from the study.

One ml aliquots of test samples were placed in sterile, screw cap polypropylene containers and placed in storage at the test temperatures of 4° C., room temperature (RT), 45° C. and 52° C.

After 10 days, the HSA-free samples stored at 4° C. and 52° C. were analyzed using polyacrylamide gel electrophoresis in the presence of sodium dodecyl sulfate (SDS-PAGE) and the 52° C. samples were analyzed by radioimmuno assay (RIA). The rEPO RIA performed on these and on other samples described in this application is a stability indicating assay. The results of the silver stained SDS-PAGE of samples stored at 4° C. showed aggregate in the cresol and chlorocresol samples. The SDS-PAGE of the samples maintained at 52° C. for 10 days showed significant aggregation present in all samples. The results were consistent with the RIA results reported in Table I below. In this table, as well as other tabulations of RIA data in this application, results are expressed as the fraction of activity remaining as compared to the starting activity.

TABLE I

| Example | pH 6 | pH 7 | +HSA, pH6 | +HSA, pH7 |
|---------|------|------|-----------|-----------|
| 1 Phenol (0.5%) | 0.12 | <0.02 | 0.20 | 0.19 |
| 2 M-Cresol (0.5%) | <0.03 | <0.01 | 0.09 | 0.07 |
| 3 Benzyl Alcohol (2%) | 0.06 | 0.07 | 0.06 | 0.10 |
| 4 Parabens (0.2%) | 0.23 | 0.10 | 0.37 | 0.26 |
| 5 Parabens (0.2%) + B.A. (0.5%) | 0.14 | 0.08 | 0.17 | 0.19 |
| 6 Chlorocresol (0.3%) | <0.01 | <0.01 | N.R. | N.R. |
| CE1 | 0.42 | 0.13 | 0.57 | 0.50 |
| CE2 | 0.33 | 0.09 | 0.54 | 0.50 |

N.R. = No Results

The HSA containing and HSA-free samples stored for 17 days at RT and 45° C. were analyzed using SDS-PAGE and either Western blotting with an anti-EPO antibody or silver staining, respectively, to monitor the stability.

The following relative rankings were observed for the amount of aggregate observed in the rEPO samples. The order of presentation is from least amount of aggregate to most aggregate reading from left to right.

| Sample | Temperature | Relative Amt. of Aggregation (Least–Most) |
|--------|-------------|-------------------------------------------|
| −HSA | Room Temp. | CE1 = CE2 < Parabens < Parabens + BA ≈ Benzyl Alcohol ≈ Phenol < Cresol < Chlorocresol |
| −HSA | 45° C. | CE1 = CE2 < Parabens < Phenol ≈ Cresol ≈ Chlorocresol ≈ Benzyl Alcohol ≈ Parabens + BA |
| +HSA | Room Temp. | CE1 = CE2 = Parabens = Phenol < Parabens + BA < Benzyl Alcohol < Cresol |
| +HSA | 45° C. | CE1 = CE2 < Phenol ≈ Cresol ≈ Benzyl Alcohol ≈ Parabens ≈ Parabens + BA |

For a given antimicrobial agent, in cases where a distinction could be made, the pH 6 sample appeared to contain less aggregate than the pH 7 sample.

RIA analysis was prepared on the HSA containing samples held for 44 days at 52° C. and the results were as shown in Table II.

TABLE II

| Example | +HSA pH6 | +HSA pH7 |
|---------|----------|----------|
| 1 Phenol (0.5%) | 0.095 | 0.036 |
| 2 M-Cresol (0.5%) | 0.057 | 0.021 |
| 3 Benzyl Alcohol (2%) | 0.051 | 0.019 |
| 4 Parabens (0.2%) | 0.106 | 0.060 |
| 5 Parabens (0.2%) + B.A. (0.5%) | 0.056 | 0.038 |
| CE1 | 0.358 | 0.194 |
| CE2 | 0.318 | 0.155 |

Examples 7–12

Samples were prepared using about 3000 U/ml rEPO, 2.5 mg/ml HSA, 100 mM sodium chloride, 20 mM sodium citrate buffer, pH 6 and the following preservatives:

| Example | Preservatives |
|---|---|
| 7 | 1% Benzyl alcohol |
| 8 | 0.18% Methyl paraben + 0.02% propyl paraben |
| 9 | 0.18% methyl paraben + 0.02% propyl paraben + 0.5% benzyl alcohol |
| 10 | 0.3% phenol |
| 11 | 0.4% phenol |
| 12 | 0.5% phenol |

To speed their solubilization the parabens were first dissolved as a concentrated solution in 1M sodium hydroxide and then diluted into a solution of citric acid and sodium chloride. The pH of the resulting mixture was adjusted to 6 with sodium hydroxide. The samples were distributed into glass vials, stoppered, and placed at RT, 37° C. and 45° C.

The solutions were tested for preservative effectiveness according to the USP Antimicrobial Preservative Effectiveness Test. All of the formulations designated as Examples 7–12 passed this test.

RIA analysis of the samples held for various times at the indicated temperatures resulted in the stability data shown in Tables III–V below.

TABLE III

| Time Temp. Example | 48 days RT | 182 days RT | 330 days RT |
|---|---|---|---|
| 7 BA | 1.14 | 1.05 | 0.64 |
| 8 Parabens | 1.07 | 1.15 | 0.73 |
| 9 Par. + BA | 0.82 | 0.85 | 0.36 |
| 10 0.3% Phenol | 0.91 | 1.10 | 0.46 |
| 11 0.4% Phenol | 1.04 | 0.94 | 0.55 |
| 12 0.5% Phenol | 0.88 | 0.71 | 0.35 |

TABLE IV

| Time Temp Example | 48 days 37° C. | 82 days 37° C. | 168 days 37° C. |
|---|---|---|---|
| 7 BA | 0.74 | 0.51 | 0.22 |
| 8 Parabens | 0.93 | 0.67 | 0.31 |
| 9 Par. + BA | 0.37 | 0.29 | 0.12 |
| 10 0.3% Phenol | 0.99 | 0.69 | 0.37 |
| 11 0.4% Phenol | 0.85 | 0.56 | 0.28 |
| 12 0.5% Phenol | 0.52 | 0.29 | 0.16 |

TABLE V

| Time Temp. Example | 48 days 45° C. | 60 days 45° C. | 82 days 45° C. | 168 days 45° C. |
|---|---|---|---|---|
| 7 BA | 0.35 | 0.21 | 0.15 | 0.03 |
| 8 Parabens | 0.57 | 0.45 | 0.32 | 0.12 |
| 9 Par. + BA | 0.18 | 0.11 | 0.08 | 0.02 |
| 10 0.3% Phenol | 0.63 | 0.46 | 0.26 | 0.10 |
| 11 0.4% Phenol | 0.36 | 0.24 | 0.23 | 0.05 |
| 12 0.5% Phenol | 0.29 | 0.12 | 0.14 | 0.02 |

The Antimicrobial Preservative Effectiveness Test was repeated on samples from Examples 7–10 after 192 days at 45° C. All of the four samples passed.

Examples 13–16

Solutions of rEPO containing 2000 and 10,000 U/ml of rEPO and preserved with 0.3% phenol were prepared. These solutions also contained 20 mM sodium citrate buffer, 100 mM sodium chloride and 0.25% HSA with the pH of the solutions adjusted to approximately 6. The solutions were placed in 2 cc and 10 cc glass containers with Teflon stoppers in the amounts indicated below:

| Example | Strength (U/ml) | Fill Volume (ml) |
|---|---|---|
| 13 | 2000 | 1.2 |
| 14 | 2000 | 10.7 |
| 15 | 10,000 | 1.2 |
| 16 | 10,000 | 10.7 |

The solutions were maintained at 2°–8° C. Stability results from RIA at various intervals are reported in Table VI. Samples were also tested periodically by SDS-PAGE and Western blot analysis to detect the formation of aggregate and breakdown of the erythropoietin. The presence of aggregate was first noted in all four of the samples at 24 months.

TABLE VI

| Time(months) Example | 6 | 9 | 12 | 18 | 24 | 30 |
|---|---|---|---|---|---|---|
| 13 | N.R. | 0.86 | 1.04 | N.R. | 0.88 | N.R. |
| 14 | 0.94 | 0.85 | 0.98 | 0.85 | 0.88 | 0.90 |
| 15 | N.R. | 0.83 | 0.97 | N.R. | 0.96 | N.R. |
| 16 | 0.95 | 0.83 | 1.06 | 0.95 | 0.99 | 0.99 |

N.R. = Not Reported

Examples 17–18

Samples of preserved erythropoietin solutions were prepared using a mixture of parabens (0.18% methyl paraben and 0.02% propyl paraben), 20 mM sodium citrate buffer, 100 mM sodium chloride, 0.25% HSA and having strengths of 2000 and 10,000 U/ml of rEPO (Examples 17 and 18 respectively). As in Examples 7–12, the parabens were first dissolved in sodium hydroxide to aid their dissolution. The pH was adjusted to a value of about 6. The samples were filled in 10 cc glass containers with Teflon stoppers to a fill volume of 10.7 ml, and were maintained at controlled room temperature and at 2°–8° C. The results of RIA analysis are reported in Table VII. At room temperature, the samples showed aggregate and breakdown visible on SDS-PAGE Western blot after 9 months. A faint indication of aggregate was noted after 24 months for the refrigerated samples.

TABLE VII

| Time (months) Exam. | Temp. | 6 | 9 | 12 | 18 | 24 | 30 | 36 |
|---|---|---|---|---|---|---|---|---|
| 17 | CRT | 0.77 | 0.76 | 0.86 | 0.68 | 0.65 | 63 | NR |
|  | 2–8° | 0.88 | 0.90 | 1.08 | 0.96 | 0.91 | 96 | NR |
| 18 | CRT | NR | 0.83 | 0.89 | NR | 0.74 | NR | 0.64 |
|  | 2–8° | NR | 0.95 | 1.19 | NR | 0.99 | NR | 1.03 |

Examples 19–20

Samples were prepared containing: 5 mM sodium citrate buffer, 140 mM sodium chloride, a mixture of parabens (0.18% methyl paraben and 0.02% propyl paraben), 0.25% HSA and 10,000 U/ml (Example 19) and 1000 U/ml (Example 20) of rEPO. The pH was adjusted to a value of about 6. A volume of 2.2 ml of Example 19 solution was filled in 3 cc glass containers with a Teflon stoppers. A volume of 10.7 ml of Example 20 solution was filled in 10 cc glass containers with a Purcoat stoppers. The solutions were stored at 2°–8° C. and the results of RIA analysis are shown in Table VIII. Analysis by SDS-PAGE Western blot revealed no aggregate or breakdown in either sample after 24 months at 2°–8° C. The Western blot of an isoelectric focusing gel shows no degradative processes such as deamidation or hydrolysis of sialic acid residues in either sample stored for 24 months at 2°–8° C. Such processes would result in an alteration of the charge on the rEPO which could be detected by isoelectric focusing.

TABLE VIII

| Time (months) Example | 6 | 12 | 24 |
|---|---|---|---|
| 19 | 1.0 | 0.98 | 1.03 |
| 20 | 1.06 | 1.01 | 1.02 |

Examples 21–25

Solutions were prepared using 1% benzyl alcohol as the preservative, 5 mM sodium citrate buffer, 140 mM sodium chloride and 0.25% HSA. Examples 21–23 and 25 contained 10,000 U/ml of rEPO while Example 24 had 1,000 U/ml. A volume of 2.2 ml of examples 21 and 23 were placed in 3 cc glass vials while 10.7 ml of examples 22, 24, and 25 was placed in 10 cc glass vials. All of the vials used Purcoat stoppers. The pH of the solutions was adjusted to a value of about 6. The samples were maintained at 2°–8° C. and the stability was analyzed using RIA analysis at periodic intervals. The results are shown in Table IX. Again, the SDS-PAGE Western blot and the isoelectric focusing Western blot showed no evidence of any degradative processes through 24 months.

TABLE IX

| Time (months) Example | 6 | 12 | 24 |
|---|---|---|---|
| 21 | 1.04 | .92 | 1.07 |
| 22 | 1.19 | 1.09 | 1.07 |
| 23 | 1.01 | 0.92 | 0.96 |

TABLE IX-continued

| Time (months) Example | 6 | 12 | 24 |
|---|---|---|---|
| 24 | 1.13 | 0.92 | 0.99 |
| 25 | 1.01 | 0.98 | 0.88 |

The USP Antimicrobial Preservative Effectiveness Test was performed on the samples of Examples 21–25 after 24 months and all samples passed the test.

As described, the invention is to a stable and preserved formulation of erythropoietin. The examples described above are illustrative of the invention, and a person skilled in the art could make changes, additions, and deletions thereto without departing from the scope of the present invention.

What is claimed is:

1. A stable pharmaceutical composition comprising a solution of a therapeutically effective amount of erythropoietin and a preservative selected from the group consisting of benzyl alcohol, a paraben and phenol or a mixture thereof.

2. The composition of claim 1 wherein the preservative is benzyl alcohol.

3. The composition of claim 1 further comprising a buffering agent.

4. The composition of claim 3 wherein the buffering agent is selected from the group consisting of citrate, phosphate, tartrate, succinate, adipate, maleate, lactate and acetate buffers, sodium bicarbonate, and sodium carbonate, or a mixture thereof.

5. The composition of claim 1 further comprising an isotonicity adjusting agent selected from the group consisting of sodium chloride, glycerol, mannitol, and sorbitol, or a mixture thereof.

6. The composition of claim 1 further comprising a pH adjusting agent which adjusts the pH of the solution to within the range 5–8.

7. The composition of claim 3 wherein the buffering agent maintains the pH of the solution within the range 5–8.

8. The composition of claim 1 further comprising an anti-adsorbent.

9. The composition of claim 8 wherein the anti-absorbent is human serum albumin, gelatin or a mixture thereof.

10. The composition of claim 1 wherein the erythropoietin is recombinant erythropoietin.

11. A stable pharmaceutical composition comprising:
   (a) an aqueous solution of erythropoietin;
   (b) a buffering agent to maintain the pH of the solution within the range 5–8; and
   (c) a preservative selected from the group consisting of benzyl alcohol, a paraben, and phenol or a mixture thereof.

12. The composition of claim 11 wherein the buffering agent is selected from the group consisting of a citrate, phosphate, tartrate, succinate, and acetate buffer, or a mixture thereof.

13. The composition of claim 11 further comprising an anti-adsorbent in an amount sufficient to reduce the loss of erythropoietin by adsorption to the walls of a container.

14. The composition of claim 11 further comprising an isotonicity adjusting agent.

15. The composition of claim 11 further comprising a pH adjusting agent which adjusts the pH of the solution to about 6.

16. The composition of claim 11 wherein the composition is not reconstituted from a lyophilizate.

17. The composition of claim 11 wherein the erythropoietin is recombinant erythropoietin.

18. The composition of claim 11 wherein the buffering agent is a citrate or phosphate buffer and the preservative is benzyl alcohol.

19. The composition of claim 11 wherein the buffering agent is a citrate or phosphate buffer and the preservative is a paraben or mixture of parabens.

20. A stable, aqueous solution of erythropoietin, comprising:

(a) a therapeutically effective amount of recombinant erythropoietin;

(b) a buffer selected from the group consisting of citrate, phosphate, tartrate, succinate, and acetate or a mixture thereof;

(c) a preservative selected from the group consisting of benzyl alcohol, a paraben and phenol or a mixture thereof;

(d) human serum albumin; and (e) an isotonicity adjusting agent.

21. The solution of claim 20 wherein the buffer is citrate and the preservative is benzyl alcohol.

22. The solution of claim 20 wherein the buffer is phosphate and the preservative is benzyl alcohol, a paraben or a mixture of parabens.

23. The solution of claim 20 wherein the buffer maintains the pH of the solution at about pH6.

24. The solution of claim 20 wherein the solution is not reconstituted from a lyophilizate.

* * * * *